United States Patent [19]

Ichikawa

[11] Patent Number: 5,377,278
[45] Date of Patent: Dec. 27, 1994

[54] METHOD AND APPARATUS FOR INSPECTING A SOLDERLESS TERMINAL BY IMAGE PROCESSING

[75] Inventor: Yoshihide Ichikawa, Yokkaichi, Japan

[73] Assignee: Sumitomo Wiring Systems, Ltd., Yokkaichi, Japan

[21] Appl. No.: 34,771

[22] Filed: Mar. 19, 1993

[30] Foreign Application Priority Data

Mar. 26, 1992 [JP] Japan .................................. 4-102240

[51] Int. Cl.$^5$ .............................................. G06K 9/00
[52] U.S. Cl. .......................................... 382/8; 348/92; 348/131
[58] Field of Search ........................ 358/106, 101, 107; 356/376, 394; 250/562; 382/1, 8, 18; 348/92, 131

[56] References Cited

U.S. PATENT DOCUMENTS

| | | | |
|---|---|---|---|
| 4,421,410 | 12/1983 | Karasaki | 356/394 |
| 4,555,799 | 11/1985 | Kodama et al. | 382/8 |
| 4,563,095 | 1/1986 | Puffer | 250/562 |
| 4,573,073 | 2/1986 | Corby, Jr. | 358/107 |
| 4,649,621 | 3/1987 | Dusel et al. | 382/8 |
| 4,734,766 | 3/1988 | Shiozumi et al. | 358/106 |
| 4,760,444 | 7/1988 | Nielson et al. | 358/106 |
| 4,922,308 | 5/1990 | Noguchi et al. | 382/8 |
| 4,975,863 | 12/1990 | Sistler et al. | 382/8 |
| 4,975,972 | 12/1990 | Bose et al. | 382/8 |
| 4,988,202 | 1/1991 | Nayar et al. | 356/376 |
| 5,010,578 | 9/1991 | Siener et al. | 358/101 |
| 5,060,290 | 10/1991 | Kelly et al. | 382/18 |
| 5,072,127 | 12/1991 | Cochran et al. | 358/106 |
| 5,073,952 | 12/1991 | Watanabe | 358/106 |
| 5,187,611 | 2/1993 | White et al. | 358/101 |
| 5,204,911 | 4/1993 | Schwartz et al. | 382/8 |
| 5,225,891 | 7/1993 | Choumei | 356/376 |
| 5,235,649 | 8/1993 | Reda | 382/18 |

FOREIGN PATENT DOCUMENTS

| | | |
|---|---|---|
| 0459489 | 12/1991 | European Pat. Off. . |
| 2553914 | 4/1985 | France . |
| 57-60249 | 4/1982 | Japan . |
| 57-060249 | 4/1982 | Japan . |
| 57-175942 | 10/1982 | Japan . |
| 60-198473 | 10/1985 | Japan . |
| 61-133845 | 6/1986 | Japan . |
| 2-189880 | 7/1990 | Japan . |
| 2047879 | 12/1980 | United Kingdom . |

OTHER PUBLICATIONS

G. Odawar et al., "An Integrated Visual System for Solder Inspection," *9th International Converence on Pattern Recognition*, 14–17 Nov. 1988, V. II. Computer Society Press.

Primary Examiner—Joseph Mancuso
Assistant Examiner—Gerard DelRosso
Attorney, Agent, or Firm—Oliff & Berridge

[57] ABSTRACT

A solderless terminal inspecting method and apparatus for determining if a solderless terminal has been satisfactorily crimped against an electric conductor has a main illuminating device for illuminating a solderless terminal having illuminating elements extending in substantially the same direction as a length of a solderless terminal. The inspecting apparatus also includes an auxiliary illuminating device for illuminating a solderless terminal in a direction opposite to the illuminating direction of the main illuminating device. The apparatus also includes an illuminated image receiving device for receiving the illuminated image of the solderless terminal. The image of the solderless terminal received by the image receiving device is binary-coded by using at least one binary level determined according to an area histogram which has been obtained in advance, and an image processing device determines from the image whether the solderless terminal is correctly crimped to the electric conductor.

19 Claims, 8 Drawing Sheets

METHOD AND APPARATUS FOR INSPECTING A SOLDERLESS TERMINAL BY IMAGE PROCESSING

BACKGROUND OF THE INVENTION

1. Field of Invention

The present invention relates to a method and apparatus for inspecting a solderless terminal which has been crimped against one end portion of an electric conductor. More specifically, the invention relates to a method and apparatus for illuminating and image processing to inspect a solderless terminal to determine whether or not the solderless terminal has been satisfactorily crimped against an electric conductor.

2. Description of the Related Art

Figure 21:
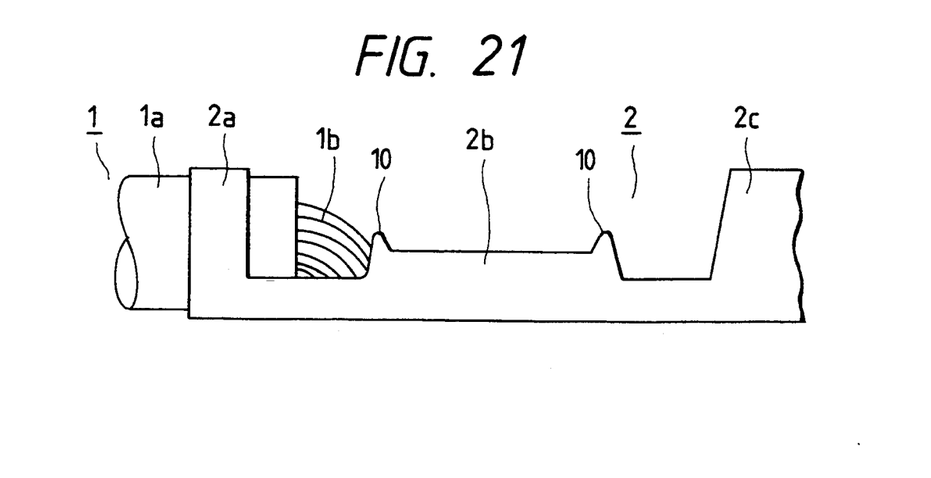
FIG. 21 is a side elevation view of a solderless terminal.
Figure 22:
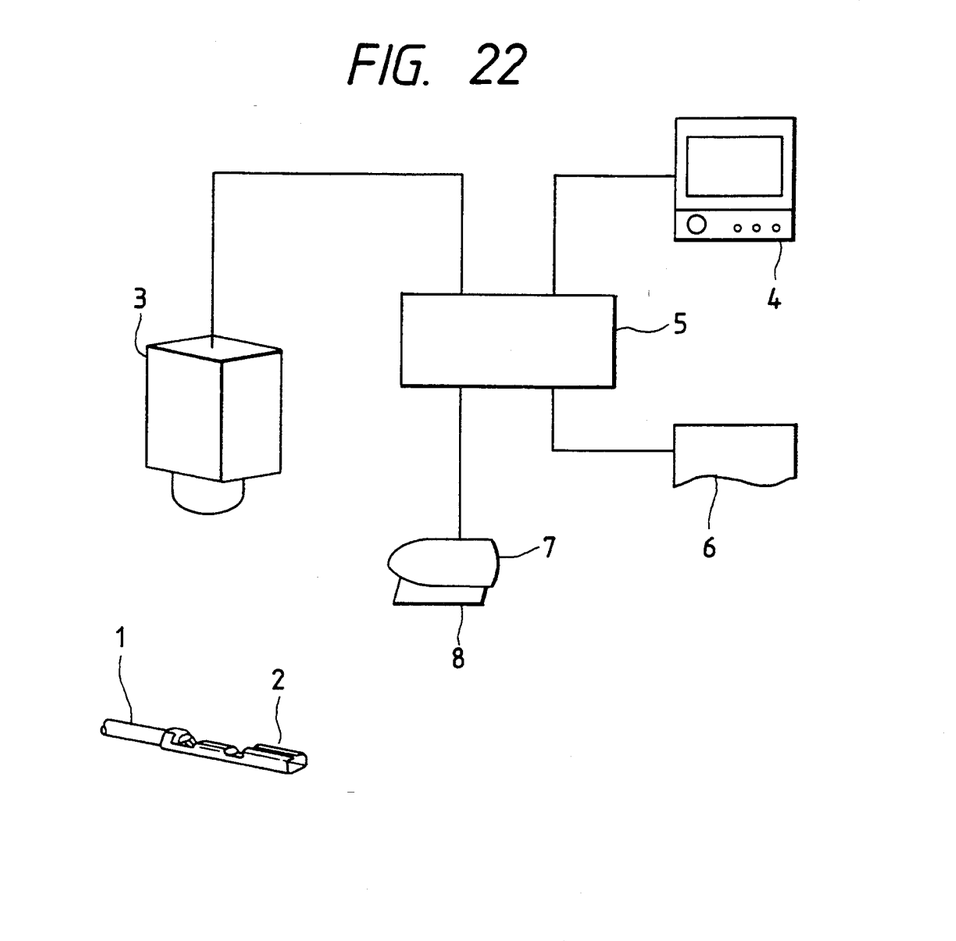
FIG. 22 is schematic view of an image processing means relating to the present invention used for inspecting solderless terminals.

FIG. 21 shows a solderless terminal 2 comprising a cylindrical shaped resin barrel 2a holding a resin cover 1a near one end portion of an electric conductor 1 which has the resin cover 1a removed, a core wire barrel 2b which also has a cylindrical shape to hold the one end portion of the electric conductor 1 having the resin cover 1a removed, a plurality of core wires 1b comprising the electric conductor 1, and an end portion 2c which is engaged with a mating solderless terminal so as to be electrically connected to the solderless terminal. As shown in FIG. 21, bell mouths 10 are formed at both ends of the core wire barrel 2b to release stress produced by crimping the solderless terminal 2 against the electric conductor 1. Heretofore, an inspecting apparatus as shown in FIG. 22 has been used in inspecting the solderless terminal 2 by image processing.

To inspect how a solderless terminal and electric conductor are crimped, the solderless terminal must first be illuminated as described later. The image of a solderless terminal 2 produced by illumination is picked up by image pick-up means 3 such as a television camera or a two-dimensional CCD camera, and displayed on a monitoring television set or monitor. The image is processed by image processing means 5, so that the resulting luminance data of the picture elements of the image are utilized to determine the presence or absence of the resin cover 1a and the core wires 1b between the resin barrel 2a and the core wire barrel 2b. The resulting luminance data is also used to determine the exposure of the core wires 1b located between the core wire barrel 2b and the end portion 2c to judge whether or not the solderless terminal 2 has been satisfactorily crimped against an electric conductor. The results of these determinations are printed out by a printer 6, or displayed on a display unit 7. Further in FIG. 22, reference numeral 8 designates an operation keyboard, with which program data or the like are inputted for an image processing operation.

In the above-described method of inspecting a crimped solderless terminal, illumination of the solderless terminal plays an important role. A variety of methods for illuminating a solderless terminal are known. For instance, Japanese Patent Application (OPI) No. 60249 (the term "OPI" as used herein means an "unexamined published application") discloses an illuminating method in which contrast is obtained by using a resin cover formed of a certain complementary color. More specifically, a spot-like convergent light beam formed by an optical fiber is applied to the solderless terminal, and the light reflected therefrom is received by image pick-up means through a filter formed a color which is the complementary color of the resin color.

Japanese Patent Application (OPI) No. 175942 discloses a method in which contrast between a resin portion and a metal portion is obtained by using polarized light. Furthermore, Japanese Patent Application (OPI) No. 198473 discloses a method in which contrast between a resin portion and a metal portion is obtained by using a light beam of a particular wavelength which the resin material readily absorbs.

The above-described conventional illuminating methods have several drawbacks. Whenever a resin color is changed, it is necessary to select either a complementary color filter suitable for the new resin color, or a light beam having a wavelength suitable for the new resin color. That is, different complementary color filters or different light beams must be used for different resin colors thereby increasing the cost and required maintenance. In addition, it is impossible for either of the illuminating methods to accurately obtain the necessary contrast between a resin portion and metal portion. Thus, the conventional methods cannot accurately determine if a solderless terminal has been satisfactorily crimped against the electric conductor.

OBJECTS AND SUMMARY OF THE INVENTION

An object of the present invention is to eliminate the above-described difficulties associated with the conventional illuminating methods for inspecting a crimped solderless terminal.

Another object of the present invention is to provide a more accurate method and apparatus for determining whether a solderless terminal has been satisfactorily crimped against an electric conductor.

Another object of the present invention is to improve the accuracy of a processed image of a solderless terminal by producing and accurately detecting a greater contrast between a resin portion and a metal portion of a solderless terminal.

According to one aspect of the invention, there is provided an illuminating apparatus for inspecting a solderless terminal by image processing. As discussed in the description of the related art, the solderless terminal comprises a resin barrel adapted to hold an end portion of an electric conductor which has its resin cover removed therefrom to expose core wires at the end. The solderless terminal further comprises a core barrel adapted to hold the exposed core wires of the electric conductor so that the electric conductor is electrically connected to the solderless terminal.

The illuminating method and apparatus of the present invention includes main illuminating means having at least one illuminating element extending substantially in the same direction as the length of the solderless terminal. In another embodiment, the main illuminating means comprises a plurality of illuminating elements arranged substantially in the same direction as the length of the solderless terminal. The main illuminating means is disposed substantially parallel to a longitudinal axis of the resin barrel and illuminates a first side the solderless terminal.

The illuminating apparatus also includes auxiliary illuminating means for illuminating a second side of the solderless terminal substantially opposite to the first side of the solderless terminal.

After the solderless terminal is illuminated by the illuminating apparatus and an image of the solderless terminal is picked up by image pick-up means from a direction substantially perpendicular to the cylindrical surfaces of the barrels, the image picked up by image pick-up means processed by image processing means to inspect how the solderless terminal has been crimped against the electric conductor.

According to another aspect of the invention, there is provided an image processing method and apparatus for inspecting a solderless terminal by image processing as described above wherein an area histogram of optical intensity of the image of the solderless terminal is obtained in advance by the image processing means. In the area histogram, binary levels are provided for a region between a specular reflection region of each of the barrels and a background region, and a region between the background region and non-specular reflection thereof. The image of the solderless terminal picked up by the image pick-up means is binary-coded by using the binary levels.

In the illuminating method of the present invention, the main illuminating means having an illuminating element extending substantially in the same direction as a length of the solderless terminal illuminates a first side of the solderless terminal. The auxiliary illuminating means illuminates a second side of the solderless terminal substantially opposite to the first side. Hence, the resin barrel and the core wire barrel of the solderless terminal, which are made of metal, provide specular reflection regions along the length of the solderless terminal and the border between the core wire barrel. The core wires at each end of the core wire barrel can be detected easily as the contrast between the resin portion and the metal part is great. Thus, the image of the solderless terminal obtained is considerably accurate. In addition, any core wire extending outside of the solderless terminal increases the contrast and thus, the accuracy of the image.

In the image processing method of the present invention, the main illuminating means and the auxiliary illuminating means illuminate the solderless terminal, and, in the area histogram obtained, the image of the solderless terminal is binary-coded by using one binary level set for the region between the specular reflection region and the background region, and another binary level set for the region between the background region and the non-specular reflection region. Therefore, in the case where any one of the core wires of the conductor extends outside of the solderless terminal, these wires can be accurately detected irrespective of the direction of extension of the core wires and thereby detect that the solderless terminal has been unsatisfactorily crimped against the electric conductor.

DETAILED DESCRIPTION OF PREFERRED EMBODIMENTS

Any solderless terminal to be inspected by the method and apparatus of the present invention is assumed to have a fundamental structure substantially similar to the one in FIG. 21. Also, the image processing means employed in the present invention is the similar to the one shown in FIG. 22. Therefore, in the following description of the invention, reference numerals used in FIGS. 21 and 22 are used to refer to identical elements in FIGS. 1–20.

Figure 1:
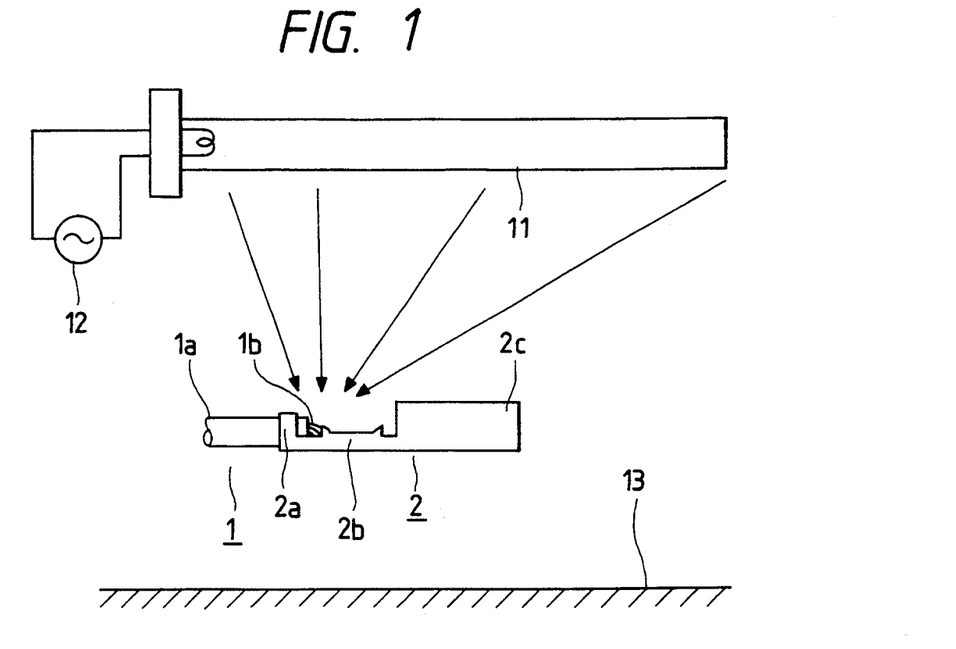
FIG. 1 is a side elevation view of a first embodiment of the solderless terminal inspecting apparatus of the present invention.
Figure 2:
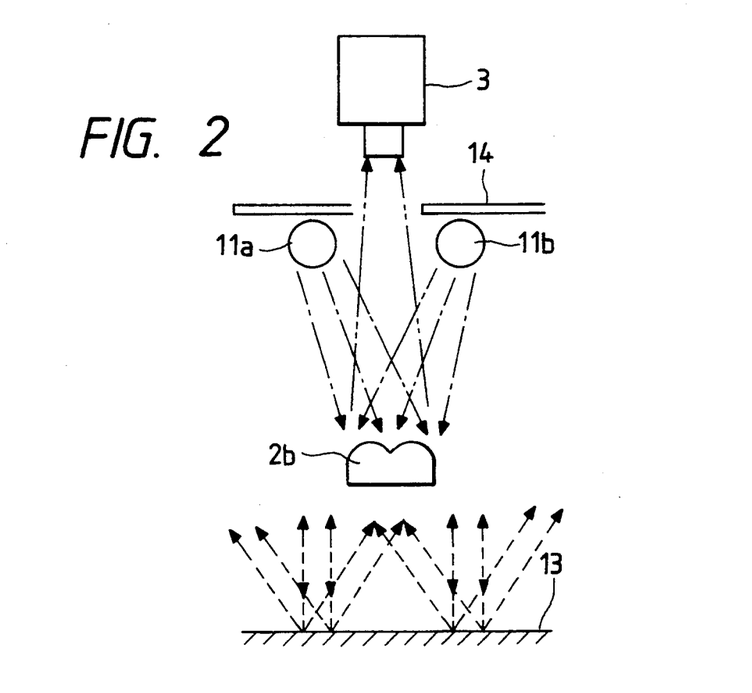
FIG. 2 is a front elevation view of the first embodiment shown in FIG. 1.

The first embodiment of the invention, as shown in FIGS. 1 and 2, comprises a main illuminating means 11 having a pair of illuminating elements 11a, 11b disposed parallel to each other. Illuminating elements 11a, 11b may comprise bar-shaped fluorescent lamps which extend longitudinally along the length of solderless terminal 2. Illuminating elements 11a, 11b are driven by a high frequency power source 12 of the order of about 20 kHz to illuminate solderless terminal 2. An auxiliary illuminating means 13 is provided for illuminating the other side substantially opposite to the side of the solderless terminal 2 illuminated by the main illumination means 11. In FIG. 1, the arrows indicate that some of the light beams are scattered, for instance, by the paint layer on the surface of main illuminating means 11 and applied to solderless terminal 2.

As shown in FIG. 2, illuminating elements 11a, 11b are arranged substantially parallel to a longitudinal axis of the resin barrel 2a, and are arranged substantially on the same side as image pick-up means 3 with respect to the solderless terminal 2. A light shielding board 14 is provided over main illuminating means 11 so that light from illuminating elements 11a, 11b is not applied directly to image pick-up means 3. Light beams emitted from illuminating elements 11a, 11b are specularly reflected by the cylindrically shaped surfaces of resin barrel 2a and core wire barrel 2b of solderless terminal 2. The light beams reflected off of resin barrel 2a and core wire barrel 2b then travel to image pick-up means 3. The illuminating light beams from illuminating elements 11a, 11b which are not reflected by solderless terminal 2 are reflected by auxiliary illuminating means 13, thus illuminating solderless terminal 2 in a direction opposite to the illumination direction of illuminating elements 11a, 11b. That is, illuminating elements 11a, 11b illuminate from a top side of solderless terminal 2 and auxiliary illuminating means 13 illuminates from a bottom side of solderless terminal 2.

Figure 3:
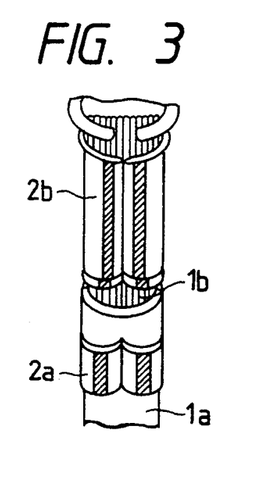
FIG. 3 is a schematic view of an image picked up by the image pick-up means of the first embodiment including specular reflection portions.
Figure 4:
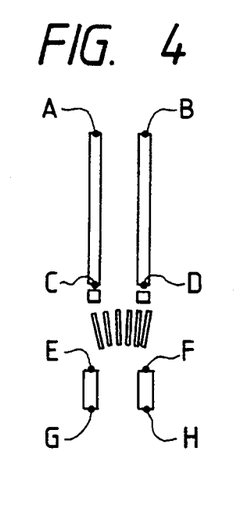
FIG. 4 is a schematic view of only the specular reflection portions of FIG. 3.

The image of solderless terminal 2 thus illuminated is shown in FIG. 3. The cross-hatched portions in FIG. 3 illustrate a distribution of specular reflections comprised of specular reflection portions. As is seen from FIG. 3, specular reflection takes place between the resin barrel 2a and the core wire barrel 2b. That is, the light beams are specularly reflected by core wires 1b exposed between barrels 2a and 2b. FIG. 4 shows those specular reflection portions only.

As was described before, bell mouths 10 are provided at both ends of core wire barrel 2b. Bell mouths 10 distinguish the borders between the specular reflection portions of core wire barrel 2b and exposed core wires 1b.

Now, the provision of image processing reference points by the image processing means 5 will be described. The image processing reference points are determined according to a run length coding method, disclosed in detail in U.S. patent application Ser. No. 07/944,984 filed by the present Applicant, the disclosure of which is hereby incorporated by reference. That is, the configuration of a solderless terminal being inspected is detected from variations in white and black data along scanning lines, as discussed in the following paragraphs.

Figure 5:
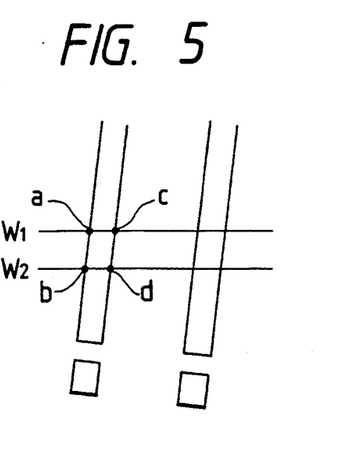
FIG. 5 is a schematic view of intersections of windows W1, W2 used to detect reference point A.

In order to determine reference points necessary for image processing, windows $W_1$ and $W_2$ in the form of straight lines as shown in FIG. 5, are provided in such a manner that they are laid across the central portion of the image of one of the specular reflection portions of core wire barrel 2b. That is, intersections a, b, c and d of the windows $W_1$ and $W_2$ and the border lines of the specular reflection portions are obtained. The gradient of the specular reflection portion can be obtained from the gradient of the segment a-b. Thereafter, a window $W_3$ is drawn in such a manner that the window $W_3$ extends from the midpoint of the segment a-c, or from any point on the segment a-c, and has the same gradient as the segment a-b. Under this condition, the point A on the window $W_3$ where luminance is changed is detected. This point A is one of the reference points necessary for image processing. Similarly, other reference points B, C, D, E, F, G and H are determined as shown in FIG. 4.

Figure 6:
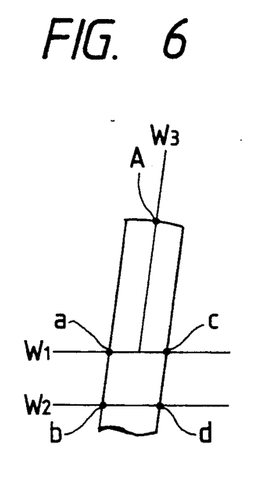
FIG. 6 is a schematic view of the detected reference point A.

In practice, barrels 2a and 2b are not completely cylindrical, and thus, less than completely specular reflections result. Therefore, the specular reflection portions are geometrically inaccurate and unstable. Hence, it is difficult to determine the reference points by performing the above-described processing operation only once as shown in FIGS. 5 and 6. That is, in order to obtain accurate reference points, the processing operation must be performed two or three times.

Figure 7:
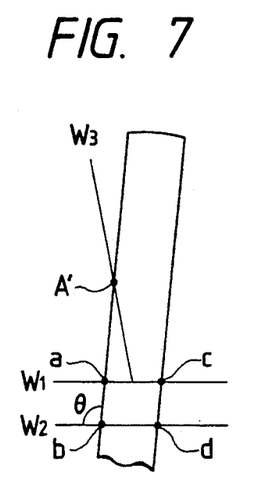
FIG. 7 is a schematic view of the detected reference point A having an inclination error angle of $\theta$.
Figure 8:
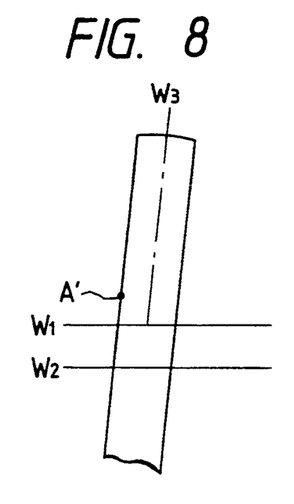
FIG. 8 is a schematic view of a shifted position of windows W1, W2 to compensate for the inclination error angle of $\theta$.

The location of the terminal 2 in FIG. 7 includes an error shown by the inclination angle $\theta$ of the segment a-b, indicating that the gradient of portion a-b may be incorrect. Therefore, if the window $W_3$ is set with an incorrect gradient as shown in FIG. 7, the reference point A' is not located at the end of the specular reflection portion. Accordingly, as shown in FIG. 8, the windows $W_1$ and $W_2$ are set in a position which is shifted as much as several picture elements in relation to the reference point A'. Then, the same processing operation is carried out again to determine whether the point on the reference window $W_3$ where luminance is changed, referred to as a luminance change point has shifted, indicating that the reference point A' was not located at the end of the specular reflection region.

Setting of the window $W_3$ and determination of the luminance change point are carried out two or three times in the above-described manner, to accurately determine the position of reference point A, which occurs when the reference point A' no longer shifts in the latest processing operation (FIG. 6).

When the reference points A through H necessary for image processing have been determined in the above-described manner, the configuration, dimension and inclination of the solderless terminal can be obtained with reference to those reference points A through H. And whether or not the state of solderless terminal 2 is acceptable is determined from the position of the end of resin cover 2a between resin barrel 1a and core wire barrel 2b. Also determined is the amount of protrusion of the core wires 1b between core wire barrel 2b and end portion 2c.

Since the reference points A through H are determined with high accuracy, it is unnecessary to hold solderless terminal 2 in one particular position with mechanical means such as a chuck. That is, it is not always necessary to accurately position the solderless terminal 1 being inspected. It is assumed that for inspection of a solderless terminal 2, solderless terminal 2 is set parallel to the X-Y plane with the width of solderless terminal perpendicular to the longitudinal direction of solderless terminal 2 set parallel to the Y-axis. It is also assumed that main illuminating means 11 and light elements 11a, 11b are arranged in the same orientation, and the image of the solderless terminal is picked up in the direction of Z-axis. In this case, solderless terminal 2 may be shifted either towards the X-axis or the Y-axis as long as it is in the visual field of image pick-up means 3. When solderless terminal 2 is shifted towards the Z-axis, the focus of image pick-up means 3 should be adjusted. It has been confirmed through experiment that, in the case of a so-called "yawing" where solderless terminal 2 turns about the Z-axis, the image can be accurately obtained even if solderless terminal 2 is displaced about ±45° from its fundamental position. In addition, it has been confirmed through experiment that, in the case of a so-called "rolling" where solderless terminal 2 turns about the Y-axis, the image can be accurately obtained even if solderless terminal 2 is displaced about ±45° from the fundamental position. Furthermore, it has been confirmed through experiment that, in the case of a so-called "pitching" where solderless terminal 2 turns about the X-axis, the image can be accurately obtained even if solderless terminal 2 is displaced ±10° to 20° from the fundamental position.

Figure 9A:
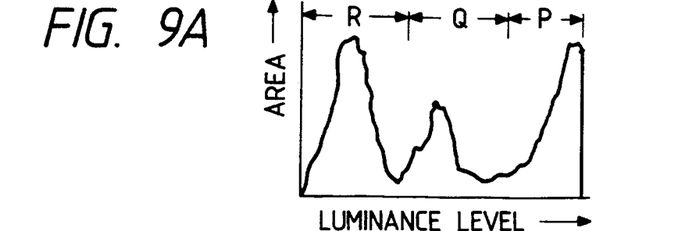
FIG. 9A is a graph of an area histogram of optical intensity corresponding to barrels 2a and 2b.

An area histogram of optical intensity of the image of solderless terminal 2 crimped against a blue electric conductor 1 is shown in FIG. 9A. In FIG. 9A, the horizonal axis represents luminance levels indicated in 256 gradations, while the vertical axis represents areas (the numbers of picture elements). The region P which displays a high luminance level corresponds to the specular reflection portions of barrels 2a and 2b. The region Q displaying a middle luminance level corresponds to the resin portion of the electric conductor 1. The region R displays a low luminance level which corresponds to a non-specular reflection portion of solderless terminal 2. Thus, in the area histogram, there is a valley between the specular reflection region P and the resin region Q, and another valley between the resin region Q and the non-specular reflection region R.

Figure 9B:
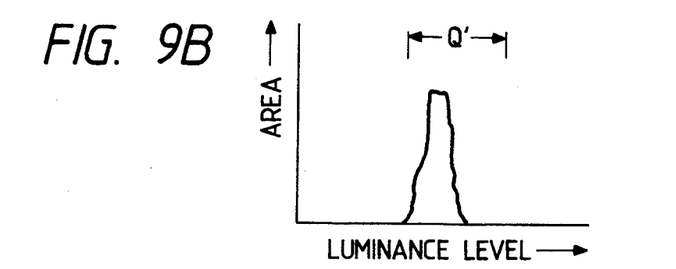
FIG. 9B is a graph of an area histogram of only the background without the solderless terminal.

An area histogram of optical intensity of the image of only the background without the solderless terminal is shown in FIG. 9B. That is, a background region Q' corresponding to the above-described resin region Q displays a peak. In this case, an irregular reflection board is selected as the auxiliary illuminating means 13 so that the background region Q' is between the specular reflection region P and the non-specular reflection region R.

Figure 9C:
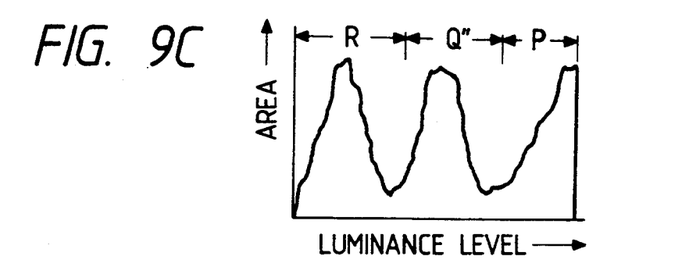
FIG. 9C is a graph of an area histogram resulting from combination of graphs of FIGS. 9A and 9B.

The area histograms shown in FIGS. 9A and 9B may be combined into the histogram shown in FIG. 9C. Similarly to FIG. 9A, the specular reflection region P, the background region Q", and the non-specular reflection region R of FIG. 9C have peaks and valleys between the regions P and Q", and between the regions Q" and R.

Hence, in the case of a blue electric conductor 1, an area histogram of a typical solderless terminal 2 is obtained in advance, and binary levels are set for the valley between the specular reflection region P and the background region Q", and the valley between the background region Q" and the non-specular reflection region R, respectively.

Figure 10A:
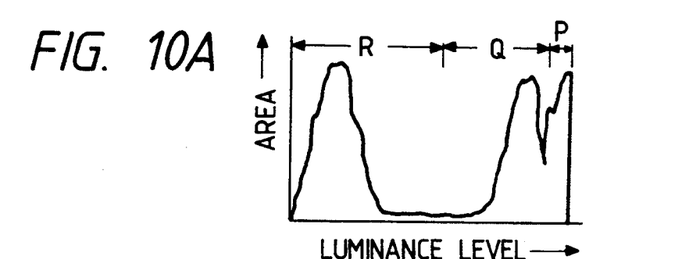
FIG. 10A is a graph of an area histogram when a white electric conductor is used.
Figure 10B:
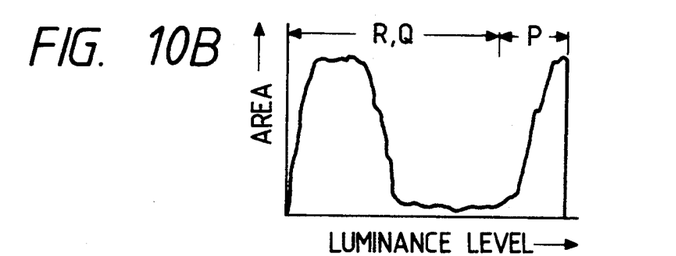
FIG. 10B is a graph of an area histogram when a black electric conductor is used.

Area histograms when a white electric conductor and a black electric conductor are used are shown in FIGS. 10A and 10B, respectively. In the case of the white electric conductor, the peak of the resin region Q is shifted towards the specular reflection region P as compared to the case of the blue electric conductor in FIG. 9A. Also, there is a small valley between the regions P and Q. In the case of the black electric conductor, the peak of the resin region Q is shifted towards the non-specular reflection region R as compared to the case of the blue electric conductor. It is impossible to distinguish the resin region Q and the non-specular reflection region R from each other.

In the case of the white electric conductor, a binary level can be set for the valley between the specular reflection region P and the resin region Q, and a binary level can be set for the valley between the resin region Q and the non-specular reflection region R by controlling the intensity of illumination. The intensity of illumination can be controlled by adjusting the aperture of the lens of image pick-up means 3. Thus, two different binary levels can be set for those valleys, and stored in the image processing means 5 shown in FIG. 22. In the case of the black electric conductor, there is a wide valley between the specular reflection region P and the region which results from the combination of the resin region Q and the non-specular reflection region R. One binary level can be set for this wide valley.

Thus, in the case of the white electric conductor 1, by obtaining an area histogram of a typical solderless terminal in advance, as in the case of the blue electric conductor, two binary levels can be set according to the area histogram obtained in advance. On the other hand, in the case of the black electric conductor, only one binary level can be set according to the area histogram. However, when necessary, another binary level can be readily set for a low luminance region according to other area histograms.

With a solderless terminal 2 illuminated by the main illuminating means 11 and auxiliary illuminating means 13 from opposite directions, two different binary levels are set according to the area histogram of optical intensity of the image of the illuminated solderless terminal. Then core wires located outside or on the side of the solderless terminal can be detected accurately.

Figure 11A:
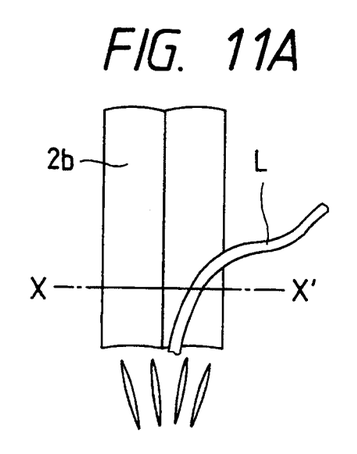
FIG. 11A is a front view elevation depicting the state where a core wire is pushed out of the core wire barrel 2b.
Figure 11B:
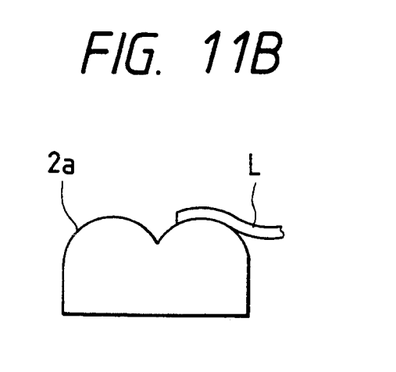
FIG. 11B is a side elevation view of FIG. 11A.
Figure 12:
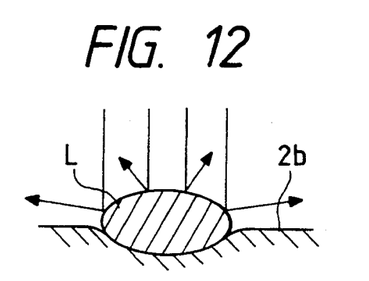
FIG. 12 is an elevation view along line X–X' of FIG. 11A.

In the case where the solderless terminal is crimped against the electrical conductor with one core wire L pushed over the top of core wire barrel 2b as shown in FIGS. 11A and 11B, rays of light from main illuminating means 11 are reflected by the core wire L as shown in FIG. 12, which is an enlarged sectional view taken along line X-X' of FIG. 11A. This is a partial irregular reflection for the specular reflection portion of core wire barrel 2b. Hence, even when solderless terminal 2 is illuminated by main illuminating means 11 only, the core wire L pushed over core wire barrel 2b can be accurately detected by binary-encoding with only one binary level. That is, a core wire pushed over core wire barrel 1b can be detected from the fact that a partial irregular reflection takes place in the specular reflection portion of core wire barrel 2b.

Figure 13:
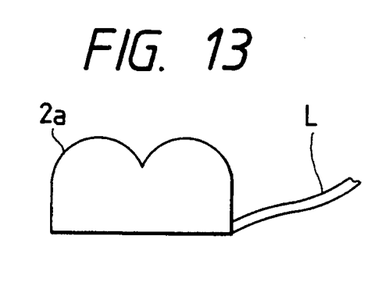
FIG. 13 is a side elevation view showing a core wire pushed out of a resin barrel.
Figure 14:
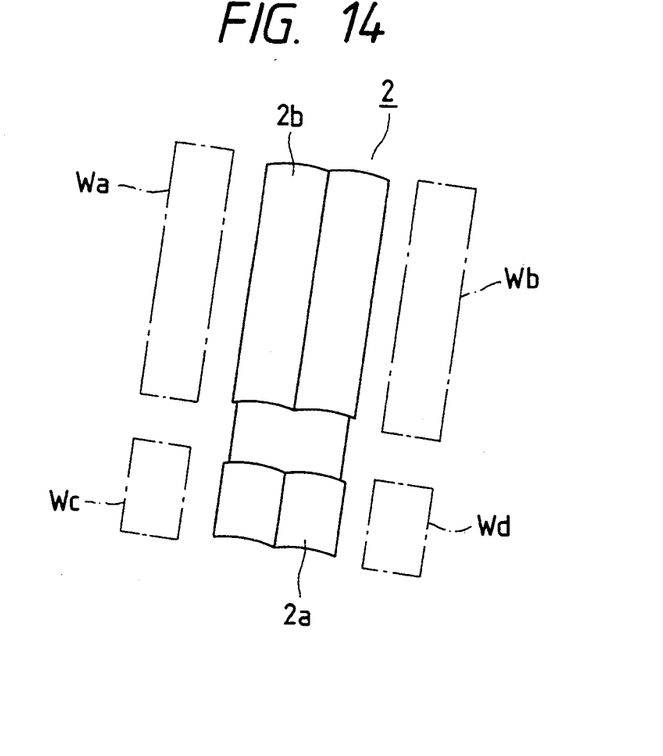
FIG. 14 is a schematic view of windows Wa, Wb, Wc and Wd.
Figure 15:
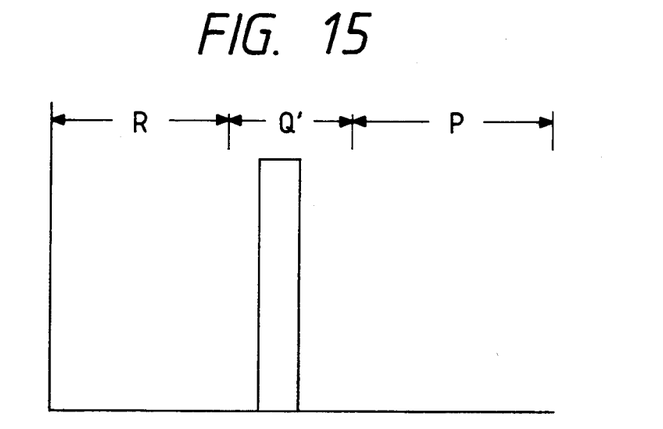
FIG. 15 is a graph of an area histogram of optical intensity of windows Wa, Wb, Wc and Wd.

On the other hand, in the case where a core wire L is pushed to the side of the solderless terminal 2 as shown in FIG. 13 and illuminated by main illuminating means only, the core wire L may or may not give rise to specular reflection. This depends on whether the core wire L is extended in the direction of the X-axis, or extended in the direction of the Y-axis, or extended in the direction of the Z-axis. Sometimes good contrast cannot be obtained because of the location of the core wire L. Thus, detection of the core wire located outside of solderless terminal 2 cannot be accomplished by processing the image with only one binary level. Therefore, the image of solderless terminal 2 is obtained by illuminating solderless terminal 2 from both sides with main illuminating means 11 and auxiliary illuminating means 13. First, as shown in FIG. 14, in the image of solderless terminal 2, rectangular windows Wa and Wb are set on both sides of core wire barrel 2b, respectively, and rectangular widows Wc and Wd are set on both sides of resin barrel 2a, respectively. If no core wire L is pushed Out, then the area histogram of optical intensity of each of the windows Wa through Wd is as shown in FIG. 15.

That is, only the background region Q' has a peak, and the remaining regions P and R have nothing.

On the other hand, if a core wire L is pushed to the side of solderless terminal 2, then in the area histogram of one of the windows Wa through Wd, the background region Q' and the region P or R have peaks. The core wire L can be detected by assigning a binary code according to the binary levels which have been set for the valley between the regions P and Q' and the valley between the regions Q' and R, to the luminance of the picture elements of the windows Wa through Wd. Thereafter, it is determined whether or not there is a picture element having a luminance value higher than the higher binary level set for the valley between the regions P and Q', and whether or not there is a picture element having a luminance value lower than the lower binary level set for the valley between the regions Q' and R. As a result of this determination, the core wire L extending outside of solderless terminal 2 can be detected irrespective of the direction in which the core wire extends.

Figure 16A:
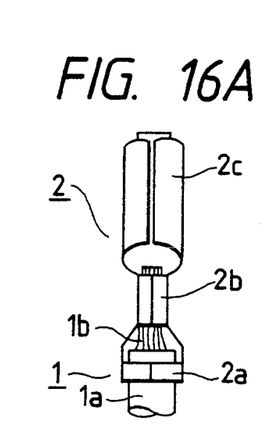
FIG. 16A is a top perspective view of a satisfactorily crimped solderless terminal.
Figure 16B:
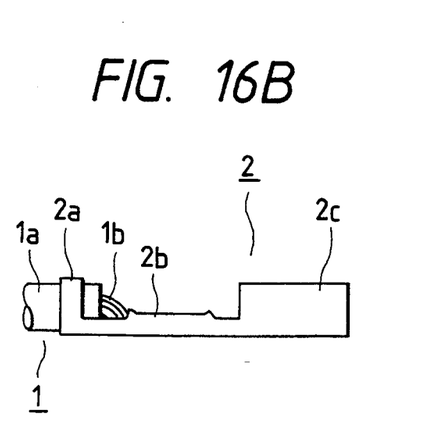
FIG. 16B is a side perspective view of FIG. 15A.

When it is determined as a result of the above-described image processing operation that, as shown in FIGS. 16A and 16B, resin barrel 2a holds resin cover 1a at a predetermined position between resin barrel 2a and core wire barrel 2b of solderless terminal 2, and core wire barrel 2b holds core wires 1b so that core wires 1b are slightly exposed between core wire barrel 2b and end portion 2c, it is decided that solderless terminal 2 has been satisfactorily crimped against electric conductor 1.

Figure 17A:
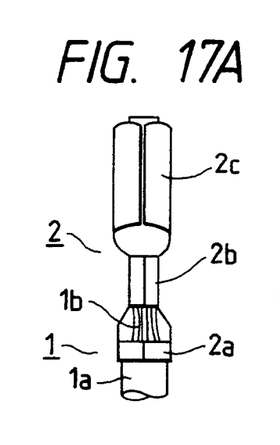
FIG. 17A is a top perspective view of an unsatisfactorily crimped solderless terminal.
Figure 17B:
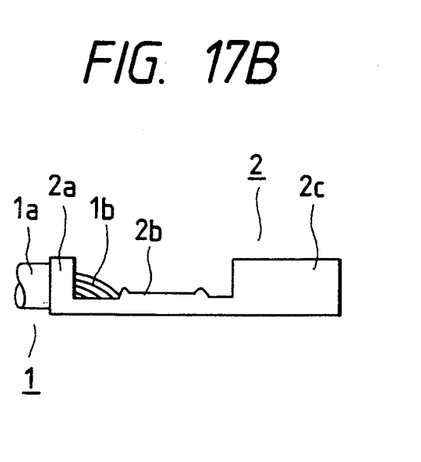
FIG. 17B is a side perspective view of FIG. 17A.

In the case where it is determined as a result of the image processing operation that, as shown in FIGS. 17A and 17B, resin cover 1a of electric conductor 1 is not located in the predetermined position between resin barrel 2a and core wire barrel 2b, and the outer end portion of resin cover 1a is held by the resin barrel 2a, then it is decided that crimping of solderless terminal 2 is unsatisfactory because resin cover 1a is not positioned and crimped satisfactorily.

Figure 18A:
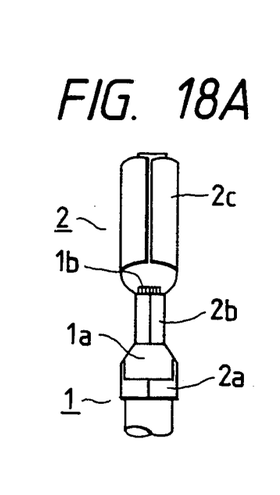
FIG. 18A is a top perspective view of an unsatisfactorily crimped solderless terminal.
Figure 18B:
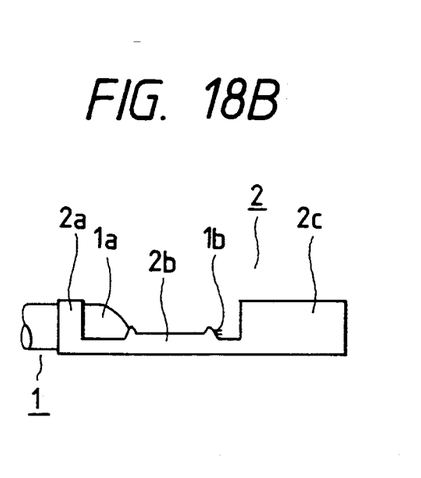
FIG. 18B is a side perspective view of FIG. 18A.

In the case where it is determined as a result of the image processing operation that, as shown in FIGS. 18A and 18B, the outer end portion of resin cover 1a is held by core wire barrel 2b of solderless terminal 2, and core wires 1b are not exposed between resin barrel 2a and core wire barrel 2b, then it is determined that crimping of solderless terminal 2 is unsatisfactory because resin cover 1a is caught by core wire barrel 2b.

In addition, as a result of the image processing operation, a variety of unsatisfactory states of the solderless terminals crimped against the electric conductors may be detected. An example of such an unsatisfactory state occurs when a core wire has been pushed out as described above and the solderless terminal has been crimped against the electric conductor from the end portion of which the resin cover has not been removed. Thus, resin barrel 2a has not been sufficiently crimped against electric conductor 1, and the core wires do not extend from the core wire barrel 2b. That is, the core wires have been cut off. Such unsatisfactory states of the solderless terminals are easily detected and can be dealt with accordingly.

When elongated main illuminating means 11 positioned in parallel alignment with solderless terminal 2 illuminates solderless terminal 2 from a direction which is substantially perpendicular to a longitudinal axis of resin barrel 2a while auxiliary illuminating means 13 illuminates solderless terminal 1 from the opposite direction, several benefits are obtained. First, since resin barrel 2a and core wire barrel 2b of solderless terminal 2, which are made of metal, have specular reflection portions extending longitudinally along the length of solderless terminal 2, the borders between core wire barrel 2b and core wires 1b are easily detected with the aid of the bell mouths 10 (FIG. 21). Also, the resulting contrast between resin cover 1a and the metal parts is high. Thus, the image of solderless terminal 1 obtained is considerably stable and accurate. Accordingly, the reference points necessary for the image processing operation can be detected with high accuracy. In addition, by binary-coding the image of solderless terminal 1 with two different binary levels, the core wire extended to the side of solderless terminal 1 can be detected accurately. That is, it can be determined with high reliability whether or not the solderless terminal has been satisfactorily crimped against the electric conductor.

Figure 19:
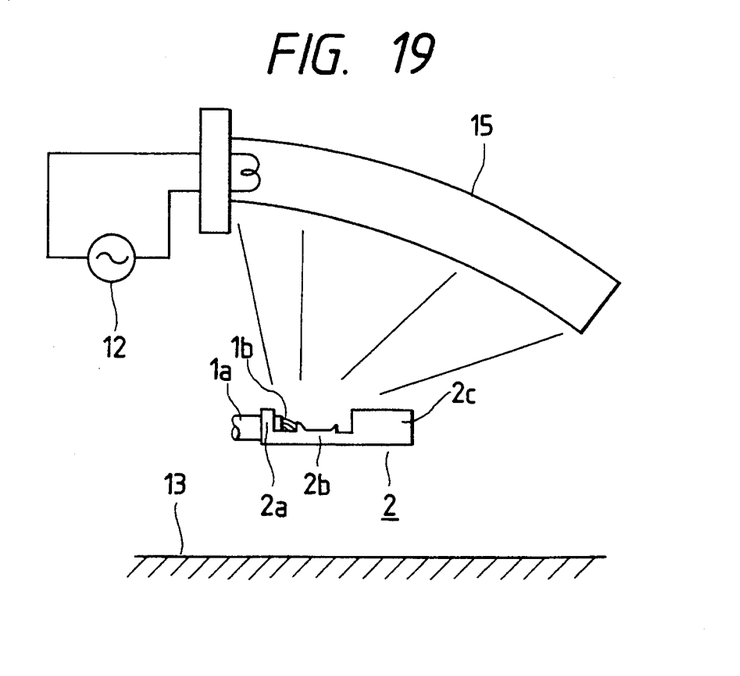
FIG. 19 is a side elevation view of a second embodiment of the solderless terminal inspecting apparatus of the present invention.

A second embodiment of the invention is shown in FIG. 19. In the second embodiment, instead of main illuminating means 11 being comprised of bar-shaped fluorescent lamps as shown in FIG. 1, main illuminating means 15 is made up of arcuate fluorescent lamps or the like. The second embodiment produces the same resulting effects as the first embodiment. Also, since the curved front end portion of main illuminating means 15 of the second embodiment is closer to solderless terminal 2 than the base end portion thereof, the bundle of rays from the main illuminating means is increased in width thereby contributing to improvement of the image processing accuracy.

Figure 20A:
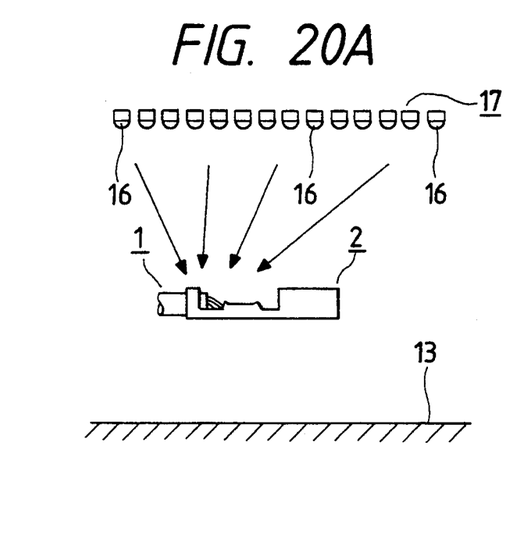
FIG. 20A is a side elevation view of a third embodiment of the solderless terminal inspecting apparatus of the present invention.
Figure 20B:
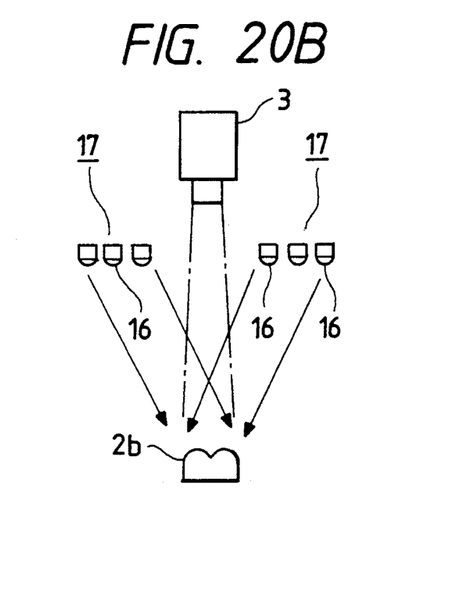
FIG. 20B is front elevation view of a third embodiment of the solderless terminal inspecting apparatus of the present invention.

A third embodiment of the invention is shown in FIG. 20. In the third embodiment, main illuminating means 17 are made up of a plurality of illuminating elements 16 such as light emitting diodes arranged in a direction which is substantially the same as the direction in which the length of solderless terminal 2 is positioned. The third embodiment produces the same effects as the first embodiment, as well as resulting in miniaturization of main illuminating means 17 and reduction of the manufacturing cost of main illuminating means 17.

In the third embodiment shown in FIG. 20, the plurality of illuminating elements 16 may be arranged arcuately as in the case of the second embodiment shown in FIG. 19.

In the above-described embodiments, the auxiliary illuminating means comprises a white irregular reflection board. However, irregular reflection boards of other colors may be employed, or a light source may be provided in addition to main illuminating means 11, 15 and 17. That is, all that is required for the auxiliary illuminating means is that, in the area histogram, the background region Q' (FIG. 9B) is between the specular reflection region P and the non-specular refection region R (FIGS. 9A and 9C).

The technical concept of the invention is applicable to inspection of all types of solderless terminals which comprise a resin barrel and a core wire barrel, and can be applied to motor vehicle harnesses or other harnesses.

What is claimed is:

1. An apparatus for inspecting a solderless terminal by image processing, the solderless terminal including a resin barrel adapted to hold an end portion of an electric conductor comprised of a plurality of core wires enclosed in a resin cover, the end portion of the electric conductor having the resin cover partially removed therefrom to expose the core wires at the end portion, a core barrel and the resin barrel adapted to hold the exposed core wires of the electric conductor to electrically connect the conductor to the solderless terminal, said apparatus for inspecting a solderless terminal comprising:

main illuminating means disposed substantially parallel to a longitudinal axis of the resin barrel for illuminating the solderless terminal from a first direction, the main illuminating means having at least one illuminating element extending substantially in the same direction as a length of the solderless terminal;

auxiliary illuminating means for illuminating a background area of the solderless terminal from a second direction substantially opposite to said first direction;

image receiving means for receiving an image of the solderless terminal produced by said main illuminating means and said auxiliary illuminating means; and image processing means for processing the image received by said image receiving means, the image processing means including means for determining whether the solderless terminal is correctly crimped to the electric conductor.

2. The apparatus of claim 1 for inspecting a solderless terminal, wherein said image is received from a direction substantially perpendicular to a longitudinal axis of the resin barrel.

3. The apparatus of claim 1 for inspecting a solderless terminal, wherein said main illuminating means comprises at least one fluorescent lamp.

4. The apparatus of claim 1 for inspecting a solderless terminal, wherein said main illuminating means comprises a plurality of light emitting diodes.

5. The apparatus of claim 1 for inspecting a solderless terminal, wherein said auxiliary illuminating means comprises a reflective board.

6. The apparatus of claim 1 for inspecting a solderless terminal, wherein said image processing means converts the image received by said image receiving means to luminance data, and said image processing means evaluates the luminance data in relation to predetermined luminance data stored in said image processing means to determine if the solderless terminal is crimped correctly.

7. The apparatus of claim 6 for inspecting a solderless terminal, wherein said image processing means comprises storing means for storing said predetermined luminance data, wherein said predetermined luminance data comprises a plurality of area histograms of optical intensities corresponding to a plurality of different color resin covers, said area histograms each containing a specular reflection region, a background region and a non-specular region, said area histograms also containing intermediate regions between the specular reflection regions and the background regions and between the background regions and the non-specular regions.

8. The apparatus of claim 7 for inspecting a solderless terminal, wherein said image processing means assigns a binary code corresponding to at least one of the intermediate regions of at least one of the area histograms stored in said storing means to the image received by said image receiving means.

9. The apparatus of claim 6 for inspecting a solderless terminal, wherein said image processing means determines if a core wire extends to the side or on top of the core wire barrel.

10. The apparatus of claim 9 for inspecting a solderless terminal, wherein said image processing means determines if a resin cover is present at the crimped end of the electric conductor.

11. The apparatus of claim 3 for inspecting a solderless terminal, wherein said fluorescent lamp is bar-shaped.

12. The apparatus of claim 3 for inspecting a solderless terminal, wherein said fluorescent lamp is arcuate-shaped.

13. The apparatus of claim 4 for inspecting a solderless terminal, wherein said main illuminating means is arcuate-shaped 14. A method for inspecting a solderless terminal by image processing, the solderless terminal including a resin barrel adapted to hold an end portion of an electric conductor comprised of a plurality of core wires enclosed in a resin cover, the end portion of the electric conductor having the resin cover partially removed therefrom to expose the core wires at the end portion, a core barrel and the resin barrel adapted to hold the exposed core wires of the electric conductor to electrically connect the conductor to the solderless terminal, said method for inspecting a solderless terminal comprising the steps of:

illuminating the solderless terminal from a first direction with a main illuminating means disposed substantially parallel to a longitudinal axis of the resin barrel and illuminating a background area of the solderless terminal from a second direction substantially opposite to said first direction;

receiving an image of the solderless terminal formed by light reflected from the illuminated solderless terminal; and processing the image received into luminance data to determine whether the solderless terminal is correctly crimped to the electric conductor.

15. The method of claim 14 for inspecting a solderless terminal, wherein the image is received from a direction substantially perpendicular to a longitudinal axis of the resin barrel.

16. The method of claim 14 for inspecting a solderless terminal, wherein said image processing step includes storing a plurality of predetermined area histograms of optical intensities corresponding to luminance data of a plurality of different color resin covers, said area histograms each containing a specular reflection region, a background region and a non-specular region, said area histograms also containing intermediate regions between the specular reflection regions and the background regions and between the background regions and the non-specular regions.

17. The method of claim 16 for inspecting a solderless terminal, wherein the image processing step further comprises selecting at least one of the plurality of predetermined area histograms and assigning a binary code corresponding to at least one of the intermediate regions of the selected at least one of the area histograms to the image received by said image receiving step.

18. The method of claim 17 for inspecting a solderless terminal, wherein said image processing step further comprises determining if a core wire extends to the side or on top of the core wire barrel.

19. The method of claim 17 for inspecting a solderless terminal, wherein said image processing step includes determining if a resin cover is not removed from the crimped end of the electric conductor.

* * * * *